US009462985B2

(12) United States Patent
Hu et al.

(10) Patent No.: US 9,462,985 B2
(45) Date of Patent: Oct. 11, 2016

(54) AUTOMATIC SELECTED HUMAN PORTION IDENTIFICATION AND ADJUSTMENT DEVICE FOR MEDICAL TREATMENT EQUIPMENT

(71) Applicant: SWISSRAY ASIA HEALTHCARE CO., LTD., Taipei (TW)

(72) Inventors: Chi Min Hu, Taipei (TW); Jian Chen Guo, Taipei (TW)

(73) Assignee: Swissray Asia Healthcare Co., Ltd., Taipei (TW)

( * ) Notice: Subject to any disclaimer, the term of this patent is extended or adjusted under 35 U.S.C. 154(b) by 120 days.

(21) Appl. No.: 14/339,525

(22) Filed: Jul. 24, 2014

(65) Prior Publication Data

US 2015/0327832 A1    Nov. 19, 2015

(30) Foreign Application Priority Data

May 14, 2014  (TW) .............................. 103116934 A

(51) Int. Cl.
*A61B 6/00* (2006.01)
*A61B 6/06* (2006.01)
*A61B 5/107* (2006.01)

(52) U.S. Cl.
CPC ............... *A61B 6/469* (2013.01); *A61B 6/06* (2013.01); *A61B 6/42* (2013.01); *A61B 6/4452* (2013.01); *A61B 6/5205* (2013.01); *A61B 6/544* (2013.01); *A61B 6/545* (2013.01); *A61B 6/547* (2013.01); *A61B 5/1079* (2013.01)

(58) Field of Classification Search
CPC ...... A61B 6/06; A61B 6/4452; A61B 6/469; A61B 6/544; A61B 6/545
USPC ........ 378/62, 63, 98.12, 146, 165, 166, 189, 378/196, 197, 205, 206
See application file for complete search history.

(56) References Cited

U.S. PATENT DOCUMENTS

| | | | | |
|---|---|---|---|---|
| 6,463,121 B1* | 10/2002 | Milnes | ................. | A61B 6/4482 378/62 |
| 6,542,579 B1* | 4/2003 | Takasawa | ................ | A61B 6/00 378/162 |
| 6,935,779 B2* | 8/2005 | Zhang | ...................... | A61B 6/08 378/196 |
| 6,942,385 B2* | 9/2005 | Fadler | ..................... | A61B 6/08 378/205 |
| 6,944,265 B2* | 9/2005 | Warp | ................... | A61B 6/4233 378/116 |
| 7,054,412 B2* | 5/2006 | Scheuering | ............ | A61B 6/589 378/108 |
| 7,114,849 B2* | 10/2006 | Atzinger | .............. | A61B 6/5241 378/206 |
| 7,142,632 B2* | 11/2006 | Atzinger | .............. | A61B 6/4225 378/196 |
| 7,522,701 B2* | 4/2009 | Jensen | ................... | A61B 6/481 378/162 |
| 7,556,427 B2* | 7/2009 | Yu | ........................ | A61B 6/4476 378/196 |
| 7,593,555 B2* | 9/2009 | Spahn | ..................... | A61B 6/00 378/115 |

(Continued)

*Primary Examiner* — Allen C. Ho
(74) *Attorney, Agent, or Firm* — Rosenberg, Klein & Lee

(57) ABSTRACT

An automatic selected human portion identification and adjustment device for medical treatment equipment is disclosed, in which an automatic selected human portion identification and adjustment device is included in the medical treatment equipment. The automatic selected human portion identification and adjustment device includes a depth camera, an image characteristic identification unit, and an X-ray detector position adjustment mechanism. The image characteristic identification unit performs image characteristic comparison between an instant image pixel depth signal with a predetermined image pixel depth signal for identification and generates, in response thereto, an X-ray detector position adjustment signal. Then, the X-ray detector position adjustment mechanism drives the X-ray detector to move in order to adjust the X-ray detector to correspond to the predetermined human body portion of a target human body.

6 Claims, 4 Drawing Sheets

(56) References Cited

U.S. PATENT DOCUMENTS

| | | | | |
|---|---|---|---|---|
| 7,654,739 B2* | 2/2010 | Lumma | A61B 6/06 | 378/116 |
| 7,684,605 B2* | 3/2010 | Klingenbeck-Regn | A61B 6/00 | 378/62 |
| 7,854,551 B2* | 12/2010 | Lv | A61B 6/447 | 378/189 |
| 7,874,729 B2* | 1/2011 | Okuno | A61B 6/4233 | 378/205 |
| 7,953,206 B2* | 5/2011 | Oogami | A61B 6/4429 | 378/98.12 |
| 8,064,572 B2* | 11/2011 | Sato | A61B 6/4429 | 378/206 |
| 8,084,744 B2* | 12/2011 | Enomoto | A61B 6/4441 | 250/370.09 |
| 8,201,999 B2* | 6/2012 | Uchida | A61B 6/4464 | 378/197 |
| 8,275,187 B2* | 9/2012 | Oogami | A61B 6/00 | 378/174 |
| 8,300,764 B2* | 10/2012 | Yamaguchi | G06T 7/0042 | 378/62 |
| 8,344,327 B2* | 1/2013 | Yamaguchi | A61B 6/5241 | 250/363.07 |
| 8,360,639 B2* | 1/2013 | Kato | A61B 6/4233 | 378/197 |
| 8,529,128 B2* | 9/2013 | Horiuchi | A61B 6/4482 | 378/196 |
| 8,755,490 B2* | 6/2014 | Takamura | A61B 6/00 | 378/108 |
| 8,767,913 B2* | 7/2014 | Okuno | A61B 6/08 | 378/206 |
| 8,873,709 B2* | 10/2014 | Kimura | A61B 6/4429 | 378/165 |
| 8,899,832 B2* | 12/2014 | Fabrizio | A61B 6/06 | 378/195 |
| 8,908,832 B2* | 12/2014 | Yamashita | A61B 6/06 | 378/62 |
| 8,950,937 B2* | 2/2015 | Okuno | A61B 6/06 | 378/114 |
| 9,149,247 B2* | 10/2015 | Lee | A61B 6/4452 | |
| 2015/0327821 A1* | 11/2015 | Hu | A61B 6/5205 | 378/62 |
| 2015/0327830 A1* | 11/2015 | Hu | A61B 6/06 | 378/8 |

* cited by examiner

AUTOMATIC SELECTED HUMAN PORTION IDENTIFICATION AND ADJUSTMENT DEVICE FOR MEDICAL TREATMENT EQUIPMENT

BACKGROUND OF THE INVENTION

1. Field of the Invention

The present invention relates to a control device of medical treatment equipment, and in particular to an automatic selected human portion identification and adjustment device combined with medical treatment equipment to control the operation of an X-ray detector of the medical treatment equipment for adjusting the X-ray detector to aligned with a predetermined selected body portion of a target human body.

2. The Related Arts

Currently, regular medical examination often applies X-ray imaging. The X-ray imaging generally uses and adjusts shielding plates to determine a radiation area. In a conventional design, a radiographer needs to manually or semi-automatically adjust the shielding plate through upward/downward and left/rightward movement in order to select a desired portion and area of the portion to be irradiated. The X-ray detector is commonly designed as a fixed device. In an alternative design, the X-ray detector is held by a hand and manually placed at the portion of human body that is to be irradiated.

In the conventional designs of the X-ray detector, a radiographer or medical personnel has to help a patient to make a correct pose and position, or a person other than the radiographer may be need to hold the X-ray detector with hands. The radiographer then proceeds to a collimator to adjust the shielding plate. This causes an issue of poor operability. Further, during the operation that a radiographer or medical personnel makes the adjustment, deviations and inconsistencies of the accuracy of adjustment, the size of the radiation area, and the radiation zone may readily occur due to difference in respect of personal experience, expertise, habit, and personal emotional issues.

When an X-ray photograph is incorrect in respect of the radiation range or radiation area, incorrect reading of visual inspection by a treating operator may occur and incorrect diagnosis may also result. Further, the chance that a patient has to take the examination once more due to the error of the operation may often be thus greatly increased. It is thus a challenge to the industry to overcome the above-discussed problems and issues.

SUMMARY OF THE INVENTION

Thus, to overcome the above-discussed problems and issues, an object of the present invention is to provide an automatic selected human portion identification and adjustment device for medical treatment equipment, in which an image characteristic identification unit receives an instant image pixel depth signal captured by a depth camera and carries out image characteristic comparison between the instant image pixel depth signal and a predetermined image pixel depth signal of a predetermined human body portion for identification and in response thereto, generates an X-ray detector position signal to allow an X-ray detector position adjustment mechanism to drive an X-ray detector of the medical treatment equipment to move along a guide mechanism thereby adjusting the X-ray detector to align with a predetermined human body portion of a target human body.

The technical solution that the present invention adopts to achieve the above object is that an automatic X-ray detector adjustment device is combined with medical treatment equipment, in which an automatic selected human portion identification and adjustment device is included in the medical treatment equipment. The automatic selected human portion identification and adjustment device includes a depth camera, an image characteristic identification unit, and an X-ray detector position adjustment mechanism. The image characteristic identification unit performs image characteristic comparison between an instant image pixel depth signal with a predetermined image pixel depth signal for identification and generates, in response thereto, an X-ray detector position adjustment signal. Then, the X-ray detector position adjustment mechanism drives the X-ray detector to move in order to adjust the X-ray detector to correspond to the predetermined human body portion of a target human body.

The automatic selected human portion identification and adjustment device for medical treatment equipment further comprises an image capture device to acquire at least one instant image of the target human body.

The automatic selected human portion identification and adjustment device for medical treatment equipment comprises a vertical carrying frame and the guide mechanism is provided on the vertical carrying frame.

The X-ray detector may be alternatively mounted to a horizontal carrying frame. The guide mechanism comprises: a first-direction guide mechanism, which is mounted to the horizontal carrying frame in a first direction, and a second-direction guide mechanism, which is mounted to the horizontal carrying frame in a second direction. The X-ray detector position adjustment mechanism comprises: a first-direction driving unit, which drives the X-ray detector to move along the first-direction guide mechanism, and a second-direction driving unit, which drives the X-ray detector to move along the second-direction guide mechanism.

The X-ray detector position adjustment mechanism may further comprise a rotation driving unit, which drives the X-ray detector to rotate about a rotation axial direction.

The automatic selected human portion identification and adjustment device for medical treatment equipment may further comprise a display device.

The efficacy is that with the above technical solution of the present invention, medical personnel, when operating an X-ray detector of an X-ray medical treatment equipment, may use the automatic X-ray detector adjustment device of the present invention to automatically detect a predetermined human body portion of a target human body, whereby errors caused by lacking of experience or poor habit of a radiographer can be reduced and the inconvenience and time required for manual adjustment of a X-ray detector by a radiographer may be greatly reduced. In addition, the difficult that a patient needs to change pose thereof to correspond to the X-ray detector can be eliminated. Further, the automatic selected human portion identification and adjustment device of the present invention is operable with a collimator control device to adjust a collimator for adjustment toward a selected human body portion.

BRIEF DESCRIPTION OF THE DRAWINGS

The present invention will be apparent to those skilled in the art by reading the following description of preferred embodiments of the present invention, with reference to the attached drawings, in which.

DETAILED DESCRIPTION OF THE PREFERRED EMBODIMENTS

Figure 1:
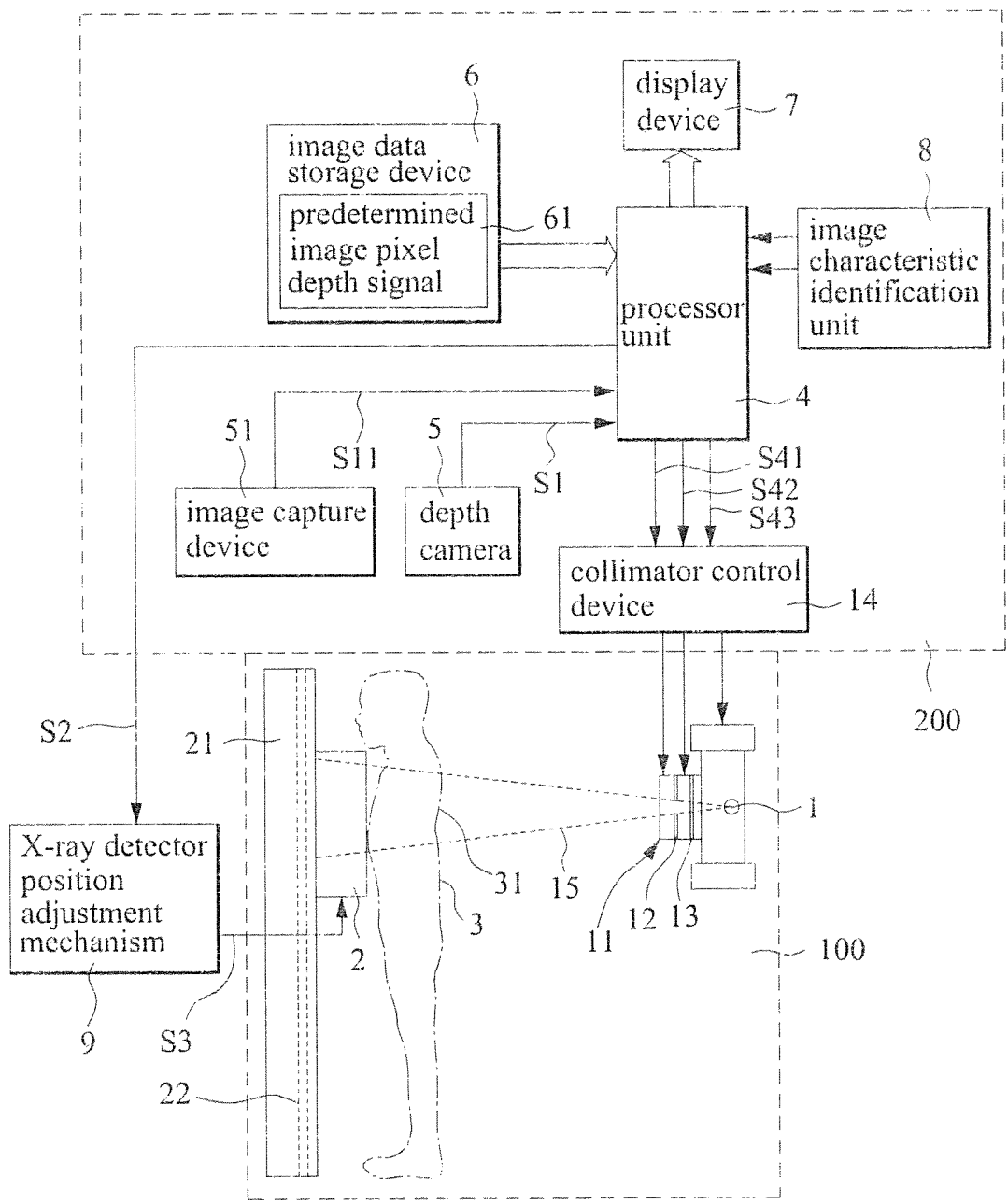
FIG. 1 is a schematic view of a circuit system of a first embodiment according to the present invention.

With reference to the drawings and in particular to FIG. 1, a first embodiment is illustrated, in which medical treatment equipment 100 is arranged to include an X-ray source generator 1, a collimator 11, and an X-ray detector 2. The X-ray source generator 1 is coupled to the collimator 11. The X-ray detector 2 is arranged at a position that is spaced from the X-ray source generator 1 by a predetermined distance. The X-ray source generator 1 emits an X-ray beam 15, which, after passing through shielding plates 12 and a filter 13 arranged in the collimator 11, is projected to a target human body 3 and is detected by the X-ray detector 2.

The collimator 11 is coupled to a collimator control device 14, whereby the collimator control device 14 controls the shielding plate 12 arranged in the collimator 11 for adjustment of a predetermined human body portion 31 of the target human body 3.

In the present invention, an automatic selected human portion identification and adjustment device 200 is combined with and coupled to the medical treatment equipment 100 to control the operation of the X-ray detector 2 of the medical treatment equipment 100 in order to execute identification of the predetermined human body portion 31 and make adjustment toward the predetermined human body portion 31 of the target human body 3.

The automatic selected human portion identification and adjustment device 200 according to the present invention comprises a processor unit 4, a depth camera 5, an image capture device 51, an image data storage device 6, a display device 7, an image characteristic identification unit 8, and an X-ray detector position adjustment mechanism 9.

The depth camera 5 is set at a position corresponding to the target human body 3 in order to acquire at least one instant image pixel depth signal S1 of the target human body 3. The depth camera 5 is connected to the processor unit 4 to transmit the acquired instant image pixel depth signal S1 to the processor unit 4.

In addition to the depth camera 5, an image capture device 51 may be provided and connected to the processor unit 4 in order to acquire at least one instant image S11 of the target human body 3 and transmit the instant image S11 to the processor unit 4.

The image data storage device 6 is connected to the processor unit 4. The image data storage device 6 stores therein at least one predetermined image pixel depth signal 61 of the predetermined human body portion 31.

The display device 7 is connected to the processor unit 4 to display the instant image pixel depth signal S1 of the target human body 3 acquired by the depth camera 5 and the instant image S11 of the target human body 3 acquired by the image capture device 51.

The image characteristic identification unit 8 is connected to the processor unit 4 for comparison and identification of characteristics. The process unit 4 compares the instant image pixel depth signal S1 acquired by the depth camera 5 and the predetermined image pixel depth signal 61 of the predetermined human body portion 31 of the image data storage device 6 for identification.

According to the result of comparison, if the instant image pixel depth signal S1 and the predetermined image pixel depth signal 61 of the predetermined human body portion 31 are different, the processor unit 4 generates, according to the difference between the instant image pixel depth signal S1 and the predetermined image pixel depth signal 61, at least one X-ray detector position adjustment signal S2 that is transmitted to the X-ray detector position adjustment mechanism 9. The X-ray detector position adjustment mechanism 9, after receiving the X-ray detector position adjustment signal S2, generates a movement driving signal S3 for driving the X-ray detector 2 to move thereby adjusting the X-ray detector 2 to correspond to the predetermined human body portion 31 of the target human body 3.

Figure 2:
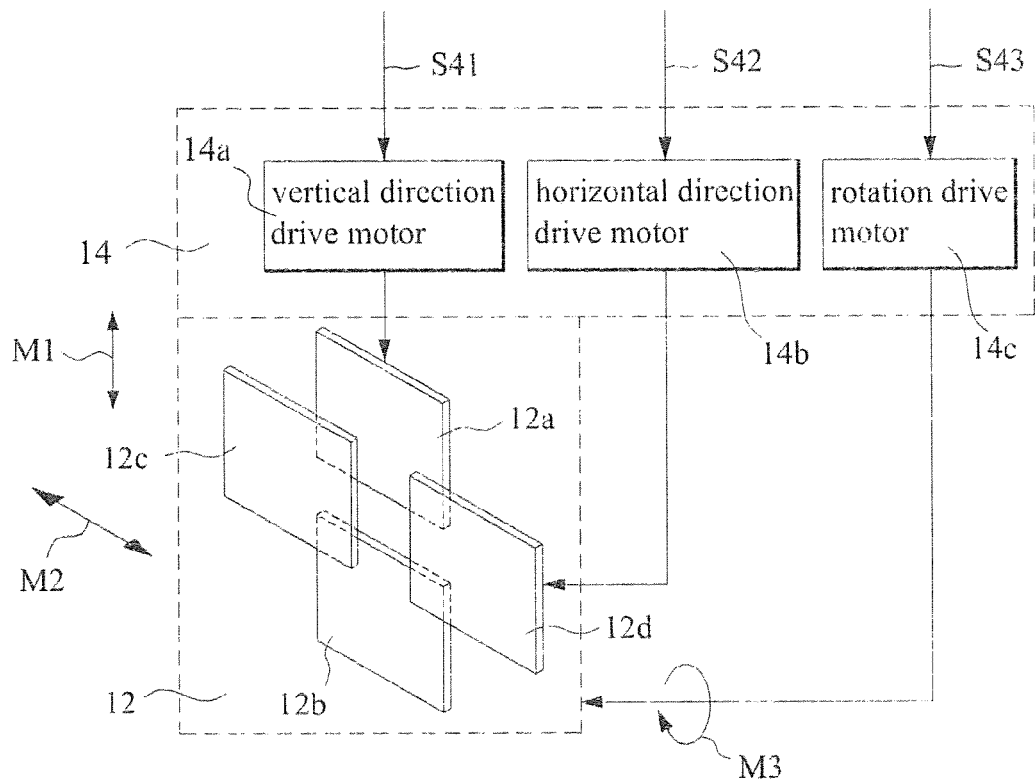
FIG. 2 is a schematic view showing a detailed circuit diagram of a collimator control device and a collimator.

As shown in FIG. 2, in an embodiment of the present invention, the collimator control device 14 comprises a vertical direction drive motor 14a, a horizontal direction drive motor 14b, and a rotation drive motor 14c. The processor unit 4 is capable of generating a vertical direction driving signal S41 to control the vertical direction drive motor 14a, a horizontal direction driving signal S42 to control the horizontal direction drive motor 14b, and a rotation driving signal S43 to control the rotation drive motor 14c respectively. The vertical direction drive motor 14a functions to drive a pair of vertical-direction arranged shielding plates 12a, 12b of the collimator 11 to move in a vertical direction M1. The horizontal direction drive motor 14b functions to drive a pair of horizontal-direction arranged shielding plates 12c, 12d of the collimator 11 to move in a horizontal direction M2. The rotation drive motor 14c functions to drive the collimator 11 to rotate about a rotation axial direction M3. With the above-discussed control, when applied in combination with X-ray detector position adjustment mechanism 9, the purpose of controlling the collimator 11 to adjust the X-ray beam 15 to align with the predetermined human body portion 31 of the target human body 3 can be achieved.

Figure 3:
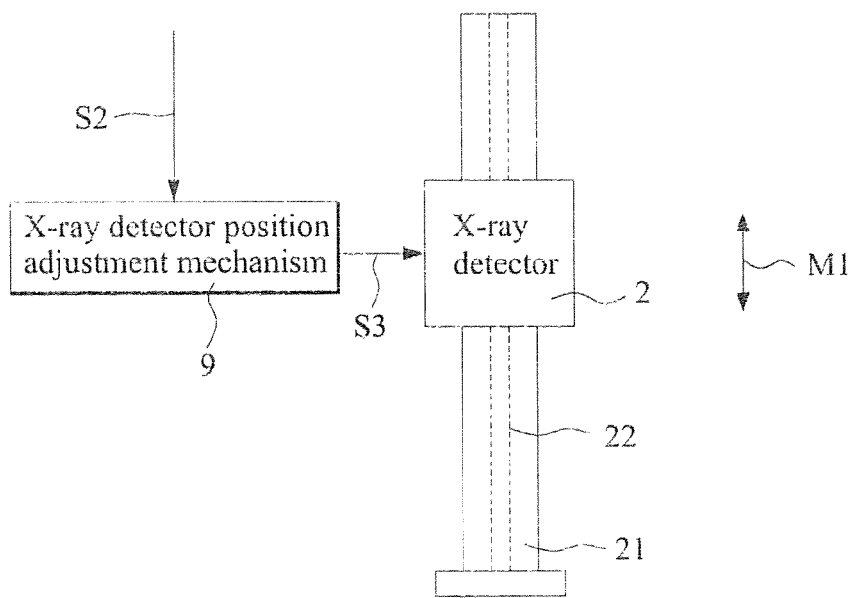
FIG. 3 is a detailed schematic view showing the coupling relationship between an X-ray detector position adjustment mechanism and an X-ray detector of FIG. 1.

As shown in FIG. 3, which shows further details of the coupling relationship between the X-ray detector position adjustment mechanism 9 and the X-ray detector 2 of FIG. 1, the X-ray detector 2 is mounted to a vertical carrying frame 21 and the vertical carrying frame 21 is provided with a guide mechanism 22. The X-ray detector position adjustment mechanism 9 receives the X-ray detector position adjustment signal S2 and generates the movement driving signal S3 to drive the X-ray detector 2, enabling the X-ray detector 2 to move in the vertical direction M1 along the guide mechanism 22. In an embodiment, the guide mechanism 22 is achieved with a conventional guide rail or guide channel. The X-ray detector position adjustment mechanism 9 may comprise a motor, a hydraulic cylinder, a pneumatic cylinder, or the like.

Figure 4:
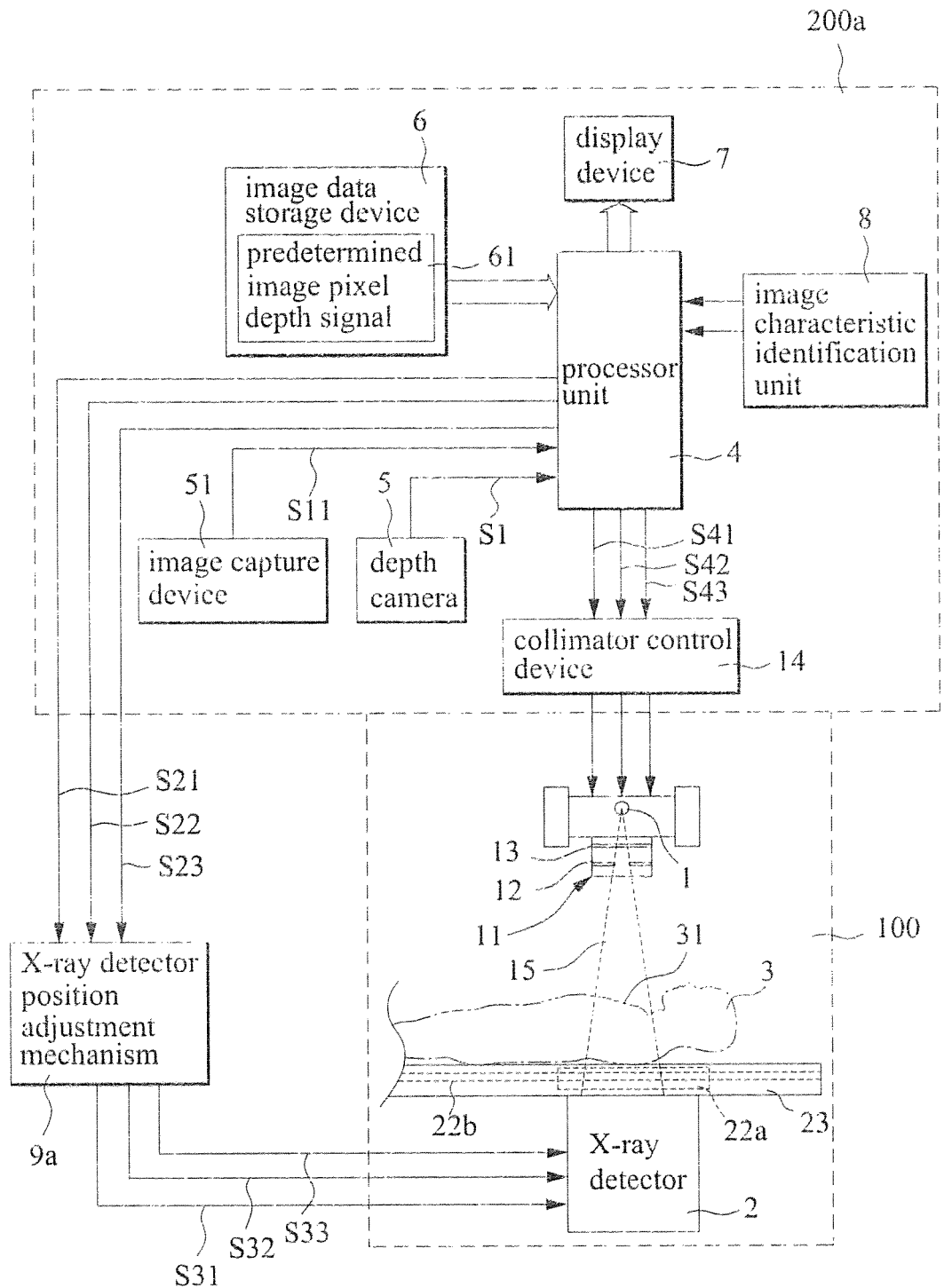
FIG. 4 is a schematic view of a circuit system of a second embodiment according to the present invention.

FIG. 4 is a schematic view showing a circuit system according to a second embodiment of the present invention. The constituent components of the instant embodiment are substantially identical to those of the first embodiment and identical components are designated with the same reference numerals for consistency. In the instant embodiment, the medical treatment equipment 100 similarly comprises an X-ray source generator 1, a collimator 11, and an X-ray detector 2. However, the collimator 11 and the X-ray detector 2 are arranged in a vertical direction and thus, the target human body 3 is allowed to lie horizontally on a treatment bed.

With the automatic selected human portion identification and adjustment device 200a according to the present invention, it is possible to control the operation of the X-ray detector 2 of the medical treatment equipment 100 in a similar way so as to achieve adjustment toward the predetermined human body portion 31 of the target human body 3.

The automatic selected human portion identification and adjustment device 200a of the instant embodiment similarly comprises a processor unit 4, a depth camera 5, an image capture device 51, an image data storage device 6, a display device 7, an image characteristic identification unit 8, and an X-ray detector position adjustment mechanism 9a.

In making a comparison, if the instant image pixel depth signal S1 and the predetermined image pixel depth signal 61 of the predetermined human body portion 31 are different, the processor unit 4 generates, according to the difference between the instant image pixel depth signal S1 and the predetermined image pixel depth signal 61 of the predetermined human body portion 31, a first-direction X-ray detector position adjustment signal S21, a second-direction X-ray detector position adjustment signal S22, and a rotation axial direction X-ray detector position adjustment signal S23 to the X-ray detector position adjustment mechanism 9a.

Figure 5:
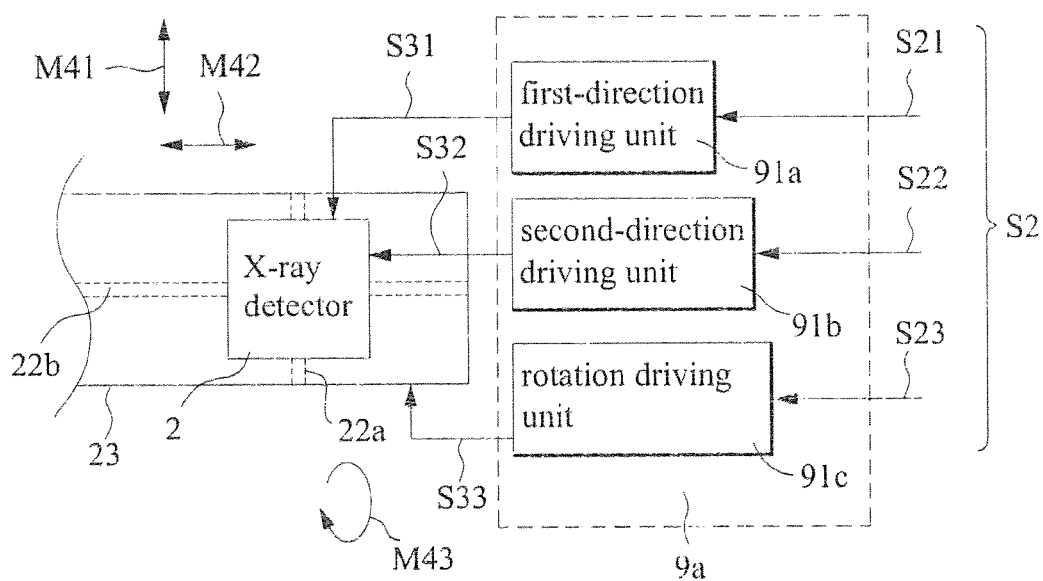
FIG. 5 is a detailed schematic view showing the coupling relationship between an X-ray detector position adjustment mechanism and an X-ray detector of FIG. 4.

As shown in FIG. 5, which shows further details of the coupling relationship between the X-ray detector position adjustment mechanism 9a and the X-ray detector 2 of FIG. 4, as shown in the drawing, a horizontal carrying frame 23 is provided with a first-direction guide mechanism 22a and a second-direction guide mechanism 22b. The first-direction guide mechanism 22a is mounted to the horizontal carrying frame 23 in a first direction M41 and the second-direction guide mechanism 22b is mounted to the horizontal carrying frame 23 in a second direction M42.

The X-ray detector position adjustment mechanism 9a receives a first-direction X-ray detector position adjustment signal S21, a second-direction X-ray detector position adjustment signal S22, and a rotation axial direction X-ray detector position adjustment signal S23 and performs the following operations:

(a) generating a first-direction driving signal S31 by activating a first-direction driving unit 91a for driving the X-ray detector 2 to move in the first direction M41 along the first-direction guide mechanism 22a;

(b) generating a second-direction driving signal S32 by activating a second-direction driving unit 91b for driving the X-ray detector 2 to move in the second direction M42 along the second-direction guide mechanism 22b; and (c) generating a rotation axial direction driving signal S33 by activating a rotation driving unit 91c for driving the horizontal carrying frame 23 to rotate about a rotation axial direction M43.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An automatic selected human portion identification and adjustment device for a medical treatment equipment, in which the medical treatment equipment includes an X-ray source generator, a collimator, an X-ray detector, and a collimator control device, wherein the X-ray source generator projects an X-ray beam to a target human body through the collimator and the X-ray detector detects the X-ray beam, comprising:

a processor unit;

an image data storage device, which is connected to the processor unit and stores therein at least one predetermined image pixel depth signal of a predetermined human body portion of the target human body;

a depth camera, which is connected to the processor unit and set at a position corresponding to the target human body to acquire at least one instant image pixel depth signal of the target human body;

an image characteristic identification unit, which is connected to the processor unit and receives the at least one instant image pixel depth signal acquired by the depth camera and compares the at least one instant image pixel depth signal with the at least one predetermined image pixel depth signal for identification in order to generate an X-ray detector position adjustment signal; and an X-ray detector position adjustment mechanism, which is connected to the processor unit and coupled to the X-ray detector to adjust a relative position of the X-ray detector with respect to the X-ray source generator, wherein the processor unit receives the X-ray detector position adjustment signal and then transmits the X-ray detector position adjustment signal to the X-ray detector position adjustment mechanism, whereby the X-ray detector position adjustment mechanism drives the X-ray detector to move so as to adjust the X-ray detector to correspond to the predetermined human body portion of the target human body.

2. The automatic selected human portion identification and adjustment device as claimed in claim 1, further comprising an image capture device to acquire at least one instant image of the target human body.

3. The automatic selected human portion identification and adjustment device as claimed in claim 1, wherein the X-ray detector is mounted to a vertical carrying frame, the guide mechanism being provided on the vertical carrying frame, the X-ray detector position adjustment mechanism driving the X-ray detector to move in a vertical direction along the guide mechanism.

4. The automatic selected human portion identification and adjustment device as claimed in claim 1, wherein the X-ray detector is mounted to a horizontal carrying frame; and the guide mechanism comprises:

a first-direction guide mechanism, which is mounted to the horizontal carrying frame in a first direction; and a second-direction guide mechanism, which is mounted to the horizontal carrying frame in a second direction; and the X-ray detector position adjustment mechanism comprises:

a first-direction driving unit, which drives the X-ray detector to move along the first-direction guide mechanism; and a second-direction driving unit, which drives the X-ray detector to move along the second-direction guide mechanism.

5. The automatic selected human portion identification and adjustment device as claimed in claim 4, wherein the X-ray detector position adjustment mechanism further comprises:

a rotation driving unit, which drives the X-ray detector to rotate about a rotation axial direction.

6. The automatic selected human portion identification and adjustment device as claimed in claim 1, further comprising a display device.

* * * * *